United States Patent
Kristensen et al.

(10) Patent No.: US 11,255,780 B2
(45) Date of Patent: Feb. 22, 2022

(54) PLANAR WAVEGUIDE DEVICE WITH NANO-SIZED FILTER

(71) Applicant: Radiometer Medical ApS, Brønshøj (DK)

(72) Inventors: Anders Kristensen, Frederiksberg C (DK); Chen Zhou, Copenhagen Ø (DK); Mehdi Keshavarz Hedayati, Kgs. Lyngby (DK); Uriel Levy, Kiryat Ono (IL)

(73) Assignee: RADIOMETER MEDICAL APS, Brønshøj (DK)

( * ) Notice: Subject to any disclaimer, the term of this patent is extended or adjusted under 35 U.S.C. 154(b) by 178 days.

(21) Appl. No.: 16/489,762

(22) PCT Filed: Feb. 28, 2018

(86) PCT No.: PCT/DK2018/050040
§ 371 (c)(1),
(2) Date: Aug. 29, 2019

(87) PCT Pub. No.: WO2018/157899
PCT Pub. Date: Sep. 7, 2018

(65) Prior Publication Data
US 2020/0240912 A1    Jul. 30, 2020
US 2021/0215603 A9    Jul. 15, 2021

(30) Foreign Application Priority Data
Mar. 1, 2017  (EP) ..................................... 17158711

(51) Int. Cl.
*G01N 21/41*  (2006.01)
*G01N 33/49*  (2006.01)
(Continued)

(52) U.S. Cl.
CPC ....... *G01N 21/4133* (2013.01); *G01N 33/491* (2013.01); *G02B 6/4291* (2013.01);
(Continued)

(58) Field of Classification Search
CPC ............. G01N 21/4133; G01N 21/552; G01N 33/491; G01N 2021/7776;
(Continued)

(56) References Cited

U.S. PATENT DOCUMENTS 5,362,445 A    11/1994   Miyahara et al.
6,903,815 B2    6/2005   Uchiyama et al.
(Continued)

FOREIGN PATENT DOCUMENTS

DE    102 41 893 A1    5/2004
EP    2 793 015 A1    10/2014
(Continued)

OTHER PUBLICATIONS

International Search Report for International Application No. PCT/DK2018/050040, dated Apr. 30, 2018 (three pages).
Written Opinion of the International Searching Authority for International Application No. PCT/DK2018/050040 (14 pages).

*Primary Examiner* — Sang H Nguyen
(74) *Attorney, Agent, or Firm* — Finnegan, Henderson, Farabow, Garrett & Dunner, LLP (57) ABSTRACT

A planar waveguide device (PWD) for interacting with a fluid (FLD) is disclosed, the planar waveguide device (PWD) comprising
 a waveguide layer (WGL) for supporting optical confinement,
 a coupling arrangement (CPA) for in-coupling and out-coupling of light into and from the waveguide layer (WGL),
 a fluid zone (FZN) for accommodating the fluid (FLD),
(Continued)

a filter layer (FTL) arranged between the fluid zone (FZN) and the waveguide layer (WGL) in an interaction region (IAR) of the waveguide layer (WGL), wherein the filter layer (FTL) comprises filter openings (FOP) arranged to allow the fluid (FLD) to interact with an evanescent field of light guided by the waveguide layer (WGL), wherein the filter openings (FOP) are adapted to prevent particles (PAR) larger than a predefined size from interacting with said evanescent field, wherein the filter openings (FOP) are arranged as line openings having their longitudinal direction in parallel with the direction of propagation (DOP) of light guided by the waveguide layer (WGL).

20 Claims, 7 Drawing Sheets

(51) Int. Cl.
*G02B 6/42* (2006.01)
*G01N 21/77* (2006.01)

(52) U.S. Cl.
CPC ........... *G01N 2021/4153* (2013.01); *G01N 2021/775* (2013.01); *G01N 2021/7709* (2013.01); *G01N 2021/7776* (2013.01)

(58) Field of Classification Search
CPC ..... G01N 2021/775; G01N 2021/4153; G01N 2021/7709; G02B 6/4291
See application file for complete search history.

(56) References Cited

U.S. PATENT DOCUMENTS

| | | | |
|---|---|---|---|
| 7,054,514 B2* | 5/2006 | Uchiyama | A61B 5/14525 356/300 |
| 7,200,311 B1 | 4/2007 | Han | |
| 7,269,308 B2* | 9/2007 | Tono | G01N 21/7703 385/12 |
| 9,297,816 B1* | 3/2016 | Pyayt | G01N 33/491 |
| 9,851,290 B2* | 12/2017 | Zhan | G01N 21/59 |
| 2002/0066978 A1* | 6/2002 | Kim | B29D 11/00346 264/259 |
| 2005/0201899 A1* | 9/2005 | Weisbuch | G01N 21/648 422/82.11 |
| 2011/0223590 A1* | 9/2011 | Chiou | G01N 21/6452 435/6.1 |
| 2014/0134602 A1* | 5/2014 | Van Zon | G01N 33/54326 435/5 |
| 2018/0364223 A1* | 12/2018 | Fretes | G01N 33/54373 |

FOREIGN PATENT DOCUMENTS

| | | |
|---|---|---|
| JP | 4-84738 A | 3/1992 |
| JP | 2003-156432 A | 5/2003 |
| JP | 2007-263736 A | 10/2007 |
| JP | 2009-085825 A | 4/2009 |
| JP | 2011-169592 A | 9/2011 |
| JP | 2013-164372 A | 8/2013 |
| JP | 2013-250193 A | 12/2013 |
| WO | WO 88/01376 | 2/1988 |
| WO | WO 2015/168776 A1 | 11/2015 |
| WO | WO 2016/168090 A1 | 10/2016 |

* cited by examiner

PLANAR WAVEGUIDE DEVICE WITH NANO-SIZED FILTER

This application is a national stage filing under 35 U.S.C. § 371 of International Application No. PCT/DK2018/050040, filed on Feb. 28, 2018, which claims priority of European Patent Application No. 17158711.6, filed on Mar. 1, 2017. The contents of these applications are each herein incorporated by reference.

FIELD OF INVENTION

The invention relates to a planar waveguide device, particularly to a planar waveguide device with a miniaturized filter, and the use thereof.

BACKGROUND

Various planar waveguide devices allowing interactions between a fluid an evanescent field from the waveguide layer are known in the art. One example is shown in US 2012/0085894 A1.

U.S. Pat. No. 7,200,311 concerns internal reflection infrared waveguides having enhanced surface sensitivity. A plurality of nanochannels may be formed in a deposited layer on top of a multiple internal reflection crystal. An index of refraction of the deposited layer can be substantially similar to an index of refraction of the multiple internal reflection crystal.

However, some problems may still exist with known planar waveguide devices, e.g. that the efficiency of the guiding of the light and the interaction with the evanescent field may be improved. Also, a robust device having a wide range of applications is desirable.

SUMMARY

The invention relates to a planar waveguide device for interacting with a fluid, the planar waveguide device comprising
  a waveguide layer for supporting optical confinement,
  a coupling arrangement for in-coupling and out-coupling of light into and from the waveguide layer,
  a fluid zone for accommodating the fluid,
  a filter layer arranged between the fluid zone and the waveguide layer in an interaction region of the waveguide layer,
wherein the filter layer comprises filter openings arranged to allow the fluid to interact with an evanescent field of light guided by the waveguide layer,
wherein the filter openings are adapted to prevent particles larger than a predefined size from interacting with said evanescent field,
wherein the filter openings are arranged as line openings having their longitudinal direction in parallel with the direction of propagation of light guided by the waveguide layer.

One advantage of the invention may be that selective interaction with a fluid is obtained by evanescent interaction with the fluid in the filter openings. In more detail, particles in the fluid are often disturbing for the interaction, e.g. if the potential for interaction is higher for the particles compared to the fluid.

A further advantage of the invention may be that the selective interaction is obtained in a fast and accurate manner. By optical interaction with the fluid, any alternative interaction including or requiring chemical reactions, filtration or separation may be avoided.

A further advantage of the invention is that it provides a very robust device which can be used for a variety of application, including sensing in otherwise problematic fluid environments where solid particles have previously disturbed or hindered accurate measurements. Also, by utilizing a waveguide adapted to support optical confinement undesirable optical leaking may be minimized or avoided. This opens up a new range of applications, especially in particle containing fluids, where the present invention may provide direct measurements without the previously needed prefiltration.

A significant advantage of the invention is that a multi-purpose sensor and interaction device for a variety of different environments may be obtained. Advantageously, the waveguide layer supports optical confinement, and thus the light is effective hindered from escaping from the waveguide layer except via the coupling arrangement, and thus at the same time also hindered in interacting with surrounding fluid, except for in the filter openings. Due to the arrangement of the filter openings according to the invention, the interaction between the light and the fluid is selectively limited to in the filter openings so as to only allow interaction where particles too large to enter the filter openings are removed. This facilitates a high degree of selectiveness, e.g. advantageous when making sensors and interaction devices for environments where particles may disturb interaction with the fluid, thus leading to a much more precise device. Particularly, it is advantageous coupling of light to the filter layer is effectively minimized or eliminated, partly due to the orientation of the filter openings, i.e. by the filter openings being arranged as line openings having their longitudinal direction in parallel with the direction of propagation of light guided by the waveguide layer, and partly due to the optical confinement, e.g. by having a filter layer with a sufficiently lower refractive index. Thus, the evanescent field should extend from the waveguide layer itself and/or an intermediate layer between the waveguide layer and the filter layer if such is present, but not from the filter layer, particularly not from the part of the filter layer outside of the filter openings, as this would allow interaction between the evanescent field and the particles that are too large to enter the filter openings. Therefore, the invention advantageously prevents interaction between the evanescent field and the particles in the fluid that are too large to enter the filter openings.

A further advantage of the invention may be that the selective interaction is obtained in a non-destructive way having the relatively little influence on the composition of the fluid. In more detail, the fluid subjected to the planar waveguide device may be substantially uninfluenced after the subjection thereto, and pre-filtering of the fluid may be avoided.

A further advantage may be that selective interaction with particles may be obtained where some particles smaller than the predefined size are interacted with but where particles larger than the predefined size are effectively excluded from interaction with the light.

Possible interactions with the fluid include absorption of the light by the fluid via the evanescent field in the filter openings, excitation of the fluid by the light via the evanescent field in the filter openings, and refractive index measurement of the fluid via evanescent field interactions with the fluid at the out-coupling. Also, light should be understood broadly, not only visible light but also infrared light including near infrared as well as ultraviolet light.

Also, the above advantage may be obtained in a relatively simple manner, by using the filter layer of the present invention.

In the present context, the optical confinement signifies optical confinement within the waveguide layer towards adjacent layers, i.e. the abutting layer on top and the abutting layer below. Of course, the optical confinement does not work at the coupling arrangement, as these effectively perform in-coupling and out-coupling of the light to and from the waveguide layer. By means of e.g. selection of the materials for the adjacent layers, e.g. an abutting filter layer on top (or alternatively another abutting layer interposed between the waveguide layer and the filter layer) and a below abutting support layer must be so, that the refractive indices of all three layers support optical confinement. Having sufficiently low refractive index in the abutting layers ensures optical confinement. The optical confinement should preferably be such that at least one optical mode is supported within the waveguide layer.

As used herein the term "planar waveguide device" is intended to mean a device for interacting with a fluid, the device incorporating a waveguide layer for guiding interaction light, i.e. light for interacting with the fluid. By using a waveguide layer, the waveguide device obtains a planar configuration, and may also be denoted a slab waveguide device.

As used herein the term "fluid" is intended to mean a liquid or a gas. It may be used with various liquids, such as e.g. blood, oil, sewage water, or liquid food ingredients, or on gasses, such as e.g. various exhaustion gasses.

As used herein the term "waveguide layer" is intended to mean a layer forming a waveguide for the applicable wavelengths of light. Typically, it is covered by an upper cladding layer on one side and a lower cladding layer on the other side, where the cladding layers may have a refractive index lower than the waveguide layer to facilitate guiding of light in the waveguide layer, i.e. optical confinement. Obviously, the refractive index here refers to the relevant wavelength(s), depending on the source of light used.

As used herein the term "coupling arrangement" is intended to mean an arrangement coupling the light in and out of the waveguide layer. It may be a single coupling element, or it may be composed of e.g. two coupling elements, an in-coupling element for coupling light into the waveguide layer and an out-coupling element for coupling light out from the waveguide layer. The coupling arrangement may include any couplers suitable for use in coupling light into the waveguide layer and out from the waveguide layer.

As used herein the term "in-coupling element" is intended to mean the part of the coupling arrangement coupling light into the waveguide layer. The in-coupling element may include any in-couplers suitable for use in coupling light into the waveguide layer.

As used herein the term "out-coupling element" is intended to mean the part of the coupling arrangement coupling light out from the waveguide layer. The out-coupling element may include any out-couplers suitable for use in coupling light out from the waveguide layer.

As used herein the term "fluid zone" is intended to mean a zone for accommodating the fluid. The fluid zone may comprise or be a fluid flow channel or a fluidic well. Such arrangements may be realized in a number of different ways; however, the important thing is that the fluid to be interacted with is allowed to contact the filter layer so as to allow interaction with the evanescent field in the filter openings.

As used herein the term "interaction region" is intended to mean the region wherein the fluid is allowed to interact with the evanescent field of the light passing through the waveguide layer. Thus, the interaction region corresponds to the region where the filter openings allow this interaction.

As used herein the term "filter openings" is intended to mean openings of the filter layer, which allows fluid to pass, but which prevents or inhibits passing of particles larger that a predefined size from passing. The filter openings are arranged as line openings, i.e. grooves, forming a grating. The dimensions of and the spacing between of the filter openings may be substantially identical, or they may vary, e.g. by gradually increasing the width of the filter openings to allow larger and larger particles to interact with the evanescent field of the light passing through the waveguide layer.

As used herein the term "particles" may refer to a variety of different particles, according to the specific use. In some embodiments particles in the fluid may have a more or less uniform size and thus all prevented from interacting with the evanescent field, whereas in other embodiments the particles may have different sizes and thus some particles smaller than the predefined size may be allowed to interact with the evanescent field.

As used herein the term "direction of propagation" is intended to refer to the direction of the light guided in the waveguide layer. For example, when the coupling arrangement comprises two separate coupling elements for in coupling an out-coupling of the light to and from the waveguide layer, respectively, the direction of propagation would be from the in-coupling element towards the out-coupling element.

As used herein the term "lower cladding layer" is intended to mean a cladding layer adjacent to the waveguide layer, on the opposite side of the waveguide layer as the filter layer. Typically, the lower cladding layer has a refractive index lower than that of the waveguide layer to support guiding of light in the waveguide layer.

As used herein the term "upper cladding layer" is intended to mean a cladding layer adjacent to the waveguide layer, on the same side of the waveguide layer as the filter layer. Typically, the upper cladding layer has a refractive index lower than that of the waveguide layer to support guiding of light in the waveguide layer. In some embodiments, the upper cladding layer and the filter layer is made from the same material; e.g. the filter layer may be formed by removing parts of an initial upper cladding covering all of the waveguide layer to create filter openings in the interaction region.

As used herein the term "grating" is intended to mean a diffractive grating, i.e. a grating that can couple light into a waveguide layer and out from the waveguide layer. Typical gratings include any regularly spaced collection of essentially identical, parallel, elongated elements. The spacing of the gratings may be adjusted to the particular wavelength(s) of light to be used.

As used herein the term "optical confinement" refers to the waveguide layer being adapted to support at least one optical mode. Typically, this may be provided by having adjacent layers, e.g. an upper cladding layer on one side and a lower cladding layer on the other side, where these layers may have a refractive index lower than the waveguide layer to facilitate guiding of light in the waveguide layer, thereby providing optical confinement.

According to an advantageous embodiment of the invention the filter openings are defined by a line spacing of at most 10 micrometer, such as at most 5 micrometer, such as at most 1 micrometer, such as at most 800 nanometer, such as at most 200 nanometer, such as at most 100 nanometer. I.e. the filter layer may be understood to be a miniaturized filter layer or a nano-sized filter layer.

According to an embodiment of the invention the filter openings are defined by a line spacing of 10 nanometer to 10 micrometer, such as 50 nanometer to 5 micrometer, such as 100 nanometer to 1 micrometer. The line spacing may also be referred to as the width of the filter openings.

According to an embodiment of the invention the filter openings have substantially the same dimensions. In other words, the line spacing is substantially the same over all the filter openings.

According to an advantageous embodiment of the invention the filter layer has a first refractive index, wherein the waveguide layer has a second refractive index, and wherein the first refractive index is lower than the second refractive index, such as at least 3 percent lower.

In other embodiments, the filter openings may have different dimensions. For example, multiple filter openings widths may be utilized in order to filter different particles sizes. The outcoupled light may for example be detected by a two-dimensional sensor array, such as a CCD or CMOS sensor, where one direction resolves the spectrum, and the other the filter opening width difference.

According to an advantageous embodiment of the invention said coupling arrangement comprises an input an in-coupling element for in-coupling of light into the waveguide layer and an out-coupling element for out-coupling of light from the waveguide layer.

One advantage of the above embodiment may be that the light is allowed to pass through the waveguide layer over a substantial distance thereby allowing interaction, such as absorption or excitation, with the fluid via the evanescent field in the filter openings.

According to an advantageous embodiment of the invention the interaction region extends between the in-coupling element and the out-coupling element.

One advantage of the above embodiment may be that the light is allowed to pass through the waveguide layer over a substantial distance thereby allowing interaction, such as absorption or excitation, with the fluid via the evanescent field in the filter openings.

According to an advantageous embodiment of the invention the interaction region extends between the in-coupling element and the out-coupling element and also over the out-coupling element.

One advantage of the above embodiment may be that the light travelling in the waveguide layer is allowed to be influence by the refractive index of the fluid during at the out-coupling element. In other words, the out-coupling of the light from the waveguide layer is influenced by the refractive index of the fluid, and by measuring this influence caused by the refractive index of the fluid, e.g. as a change of deflection of the outcoupled light and/or as a change of wavelength of the light at a fixed position, a measure of the refractive index may advantageously be obtained. This embodiment may advantageously allow for interaction between the evanescent field and the fluid by absorption of light or excitation by light at the same time as obtaining a measure of the refractive index of the fluid.

Using a grating as the out-coupling element provides dispersion of the light facilitating the measurement of the refractive index of the fluid.

According to an advantageous embodiment of the invention said coupling arrangement extends over at least part of the interaction region, such as over the whole of the interaction region.

One advantage of the above embodiment may be that the refractive index of the fluid may be obtained. By allowing the fluid to interact with the evanescent field of the light at the coupling arrangement, i.e. also at the position of the out-coupling of the light, the out-coupling of the light from the waveguide layer is influenced by the refractive index of the fluid, and by measuring this influence caused by the refractive index of the fluid, e.g. as a change of deflection of the outcoupled light and/or as a change of wavelength of the light at a fixed position, a measure of the refractive index may advantageously be obtained.

Using a grating as the out-coupling element provides dispersion of the light facilitating the measurement of the refractive index of the fluid.

According to an advantageous embodiment of the invention the out-coupling element comprises a dispersive element, such as a grating.

One advantage of the above embodiment may be that the dispersive element, e.g. the grating, may cause diffractive deflection of the light and thereby out-coupling of the light from the waveguide. This diffractive deflection is obtained in a wavelength dependent manner; i.e. different wavelengths are deflected in different angles. Especially when combined with embodiments where the interaction region is allowed to extend, at least partly, over the out-coupling element, this advantageously allows measurement of the reflective index of the fluid, since the dispersive action, i.e. the angle of out-coupling, is influence by the reflective index of the fluid. Thus, by measuring this influence caused by the refractive index of the fluid, e.g. as a change of deflection of the outcoupled light and/or as a change of wavelength of the light at a fixed position, a measure of the refractive index may advantageously be obtained As illustrated above, the coupling arrangement may in some embodiments comprise a separate in-coupling element and out-coupling element. In other embodiments, the coupling arrangement works to both couple light into the waveguide layer and couple the light out from the waveguide layer, i.e. both as an in-coupling element and an out-coupling element.

Alternatively, the out-coupling element may be a prism based out-coupling element, or direct coupling to an optical fiber.

According to an embodiment of the invention, the in-coupling element comprises a grating, a prism, or a direct coupling to an optical fiber.

According to an embodiment of the invention the planar waveguide layer further comprises an upper cladding layer. The upper cladding layer may cover the waveguide layer outside the filter layer. In some embodiments the filter layer may be the same layer as the upper cladding layer, where the filter layer is formed by creating openings in the upper layer thereby forming the interaction region. Typically, the upper cladding layer may have a lower refractive index than the waveguide layer, e.g. at least 0.2 units lower refractive index.

According to an embodiment of the invention the waveguide layer is deposited on a lower cladding layer having a lower refractive index, such as at least 0.2 units lower refractive index.

It should be understood that the planar waveguide device may comprise a light source or may receive light from an external light source.

According to an advantageous embodiment of the invention the planar waveguide device further comprises a laser device as a light source.

One advantage of the above embodiment may be that it enables detection of light by an array based light sensor to give information about influence on the light, such as influence by the refraction index of the fluid at the out-coupling from the waveguide layer.

According to an advantageous embodiment of the invention the planar waveguide device further comprises a broadband light source as a light source.

One advantage of the above embodiment may be that it enables a spectrometric detection of wavelength at a fixed position to give information about influence on the light, such as influence by the refraction index of the fluid at the out-coupling from the waveguide layer.

For example, the broadband light source may have a width extending over the whole of the visible spectrum of light, e.g. as taken from 400 to 700 nanometers, i.e. a white light source.

According to an advantageous embodiment of the invention the planar waveguide device further comprises an array based light sensor, such as a CMOS sensor, CCD sensor or photodiode array sensor.

One advantage of the above embodiment may be that detection of light from a laser device by an array based light sensor may give information about influence on the light, such as influence by the refraction index of the fluid at the out-coupling from the waveguide layer.

In this context a CMOS sensor and a CCD sensor are each considered as an array comprising a number of pixels.

Using a dispersive element, such as a grating, the light outcoupled may be separated into its wavelength components.

When an array based light sensor is used with a laser light source and using a dispersive element, such as a grating, as the out-coupling element, fluid interactions with the out-coupling, facilitated by the interaction region covering, at least partly, such as fully, the out-coupling element or the whole coupling arrangement, can be detected by detecting the out-coupling angle of the light.

When an array based light sensor is used with a broadband light source interaction between the fluid and the out-coupling leads to a different wavelength of outcoupled light at a particular fixed position of the light sensor. Thus, using an optical spectrometer as the light sensor, the detected wavelength of outcoupled light gives an indication of the interaction with the fluid and thus the refractive index of the fluid.

According to an embodiment of the invention the planar waveguide device further comprises a photodiode as a light sensor.

According to an advantageous embodiment of the invention the planar waveguide device further comprises an optical spectrometer as a light sensor.

One advantage of the above embodiment may be that spectrometric detection of wavelength of light at a fixed position to give information about influence on the light, such as influence by the refraction index of the fluid at the out-coupling from the waveguide layer. By using a broadband light source, a sufficient range of available wavelengths enables detection of light by the optical spectrometer for fluids having a sufficient range of refractive indices.

According to an advantageous embodiment of the invention the fluid is a liquid, such as blood.

In embodiments where the liquid is blood, the particles may be red blood cells, particularly, when the planar waveguide device is to function as a blood hemolysis sensor.

One advantage of the above embodiments may be that an indication of the level of blood hemolysis may be obtained by absorption measurements with wavelengths absorbed by hemoglobin.

Further possible liquids, according to various embodiments, include e.g. waste water, engine oil, food ingredients, etc.

According to an advantageous embodiment of the invention the planar waveguide device further comprises a fluid flow channel forming the fluid zone.

According to an advantageous embodiment of the invention the fluid flow channel is a flow cell.

According to an advantageous embodiment of the invention the planar waveguide device further comprises a cladding layer abutting the waveguide layer on the opposite side of the filter layer, the cladding layer having a third refractive index, wherein the third refractive index is lower than the second refractive index, such as at least 3 percent lower.

According to an embodiment the filter layer comprises or consists of UV curable polymer (OrmoComp). Other ORMOCER polymers may also be used. Also, epoxy polymer like SU8, or other UV curable resists, like acrylic UV resists, or any other nano imprint resists may be used. The important thing is that the material is relatively cheap, can be shaped one way or another, and is hard and durable—so it will resist influence by the particles, and resist the chemistry of the fluid. The waveguide layer may for example be comprise or be composed of silicon.

Various known methods may be used to create the filter layer, for example various suitable imprint processes including UV-nanoimprint processes, thermal imprint processes, and UV-thermal-hybrid imprint processes.

According to an embodiment of the invention, an intermediate layer is interposed between the waveguide layer and the filter layer. The intermediate layer may function as a protective layer for the waveguide layer against the fluid and/or it may facilitate selective bonding of certain molecules or substances in the fluid to increase interaction with the evanescent field.

The invention further relates to the use of a planar waveguide device according to the invention and any of its embodiments for detecting blood hemolysis.

An indicator of blood hemolysis is presence of free hemoglobin in the blood plasma. This free hemoglobin comes from rupturing of red blood cells, this rupturing is known as blood hemolysis and may be an indicator of the condition of a patient. However, since hemoglobin is also present in the red blood cells, these would typically have to be separated away from the blood plasma to measure the remaining hemoglobin in the blood plasma. Also, the manipulation of the blood, e.g. during filtering, may itself lead to further hemolysis and further free hemoglobin. Since the measured hemoglobin is composed both from hemoglobin from the patient condition induced hemolysis and further hemolysis not related to the patient's condition, the result may be inaccurate or even unusable.

However, by means of the planar waveguide device of the present invention, the free hemoglobin may be measured without any pre-filtering of the red blood cells, since these are kept out of interaction by the filter layer, and thus a far more accurate result may be obtained.

Various other uses of the planar waveguide device of the invention and any of its embodiments may include absorption measurement, measurements of refractive index of a fluid, and for excitation of the fluid and/or components thereof.

The invention further relates to a method of interacting light with a fluid, the method comprising the steps of
coupling light into a waveguide layer,
guiding light within the waveguide layer forming an evanescent field outside the waveguide layer,
interacting an evanescent field of guided light with the fluid,
filtering the fluid so as to prevent particles larger than a predefined size from interacting with said evanescent field using a filter layer comprising filter openings arranged to allow the fluid to interact with an evanescent field of light guided by the waveguide layer,
coupling interacted light out from the waveguide layer,
wherein the filter openings are arranged as line openings having their longitudinal direction in parallel with the direction of propagation of light guided by the waveguide layer.

According to an advantageous embodiment of the invention the method further comprises the step of measuring at least one characteristic of the outcoupled light.

According to an advantageous embodiment of the invention the fluid comprises particles larger than said predefined size.

According to an advantageous embodiment of the invention the method is performed using the planar waveguide device of the invention or any of its embodiments.

According to an advantageous embodiment of the invention the planar waveguide device is adapted to be operable with the method of the invention or any of its embodiments.

THE FIGURES

The invention will now be described with reference to the figures where.

DETAILED DESCRIPTION

Figure 1:
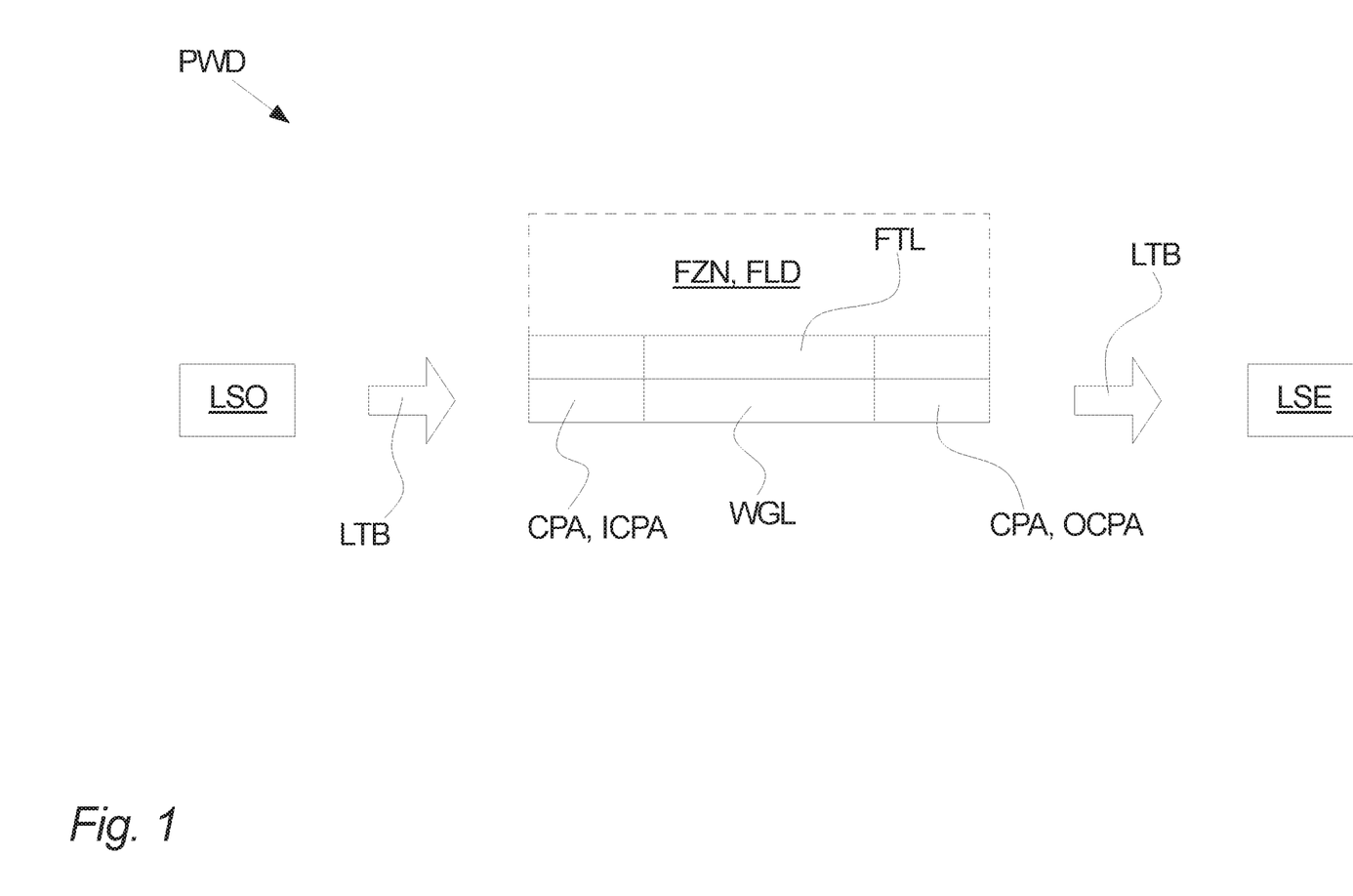
FIG. 1 illustrates a general planar waveguide device according to an embodiment of the invention.

Referring to FIG. 1, a schematic view of a planar waveguide device PWD according to an embodiment of the invention is shown. The planar waveguide device PWD is adapted for allowing interaction between a fluid FLD and a light beam LTG. This is done by means of a filter layer FTL, as described in more detail below.

Further embodiments are illustrated in more detail on FIGS. 2-6, and all of these embodiments may be understood in the light of FIG. 1 and the discussion thereof below.

Returning to FIG. 1, the planar waveguide device PWD comprises a waveguide layer WGL for supporting optical confinement, a coupling arrangement CPA, a fluid zone FZN for accommodating the fluid FLD, and a filter layer FTL.

The filter layer FTL is nano-sized in the sense that the width of the filter openings FOP may typically be at most 10 micrometer, such as at most 5 micrometer, such as at most 1 micrometer, such as at most 800 nanometer, such as at most 200 nanometer, such as at most 100 nanometer.

The planar waveguide device PWD may further comprise a light source LSO and a light sensor LSE. The light source LSO emits a light beam LTB, e.g. a laser beam from a laser device or a broadband light beam from a broadband light source.

The coupling arrangement CPA is adapted for in-coupling and out-coupling of light of the light beam into and from the waveguide layer WGL. In FIG. 1, the coupling arrangement CPA comprises a separate in-coupling element ICPA and a separate out-coupling element OCPA; however, in other embodiments the coupling arrangement CPA may be formed by a single coupling element CPA performing both the in-coupling and out-coupling of the light into and from the waveguide layer WGL. The coupling arrangement CPA may comprise a grating, a prism, or a direct coupling to an optical fiber.

The filter layer FTL comprises filter openings FOP arranged to allow the fluid FLD to interact with an evanescent field of light guided by the waveguide layer WGL.

The filter layer FTL is arranged between the fluid zone FZN and the waveguide layer WGL in an interaction region IAR of the waveguide layer WGL. Thereby, the filter openings FOP can prevent particles PAR larger than a predefined size from interacting with said evanescent field. The predefined size is typically determined by the width of the filter openings FOP, which are in the nano-scale region, e.g. at most 10 micrometer. In other words, the filter layer FTL separates the fluid zone FZN from the waveguide layer WGL, in the sense that in controls passage of material between the two. The planar waveguide device PWD may sometimes comprise a further layer between the filter layer FTL and the waveguide layer WGL, e.g. to provide protection of the waveguide layer WGL or to provide selective bonding to e.g. antibodies, polymers, aptamers or other receptors for binding of specimen in the fluid. However, the further layer must be arranged to allow the evanescent field to extend into the fluid.

Further to the above it should be understood that interactions with said evanescent field interactions are in the filter openings FOP. I.e. by allowing the fluid FLD to enter into the filter openings FOP, the fluid FLD is allowed to interact with the evanescent field, and by preventing particles PAR larger than a predefined size from entering the filter openings FOP, the particles PAR are prevented from interacting with said evanescent field.

The filter openings FOP are arranged as line openings having their longitudinal direction in parallel with the direction of propagation DOP of light guided by the waveguide layer WGL. This is illustrated more clearly in some the following figures, e.g. FIGS. 5-6. Thereby, the filter layer FTL is optically decoupled from the waveguide in the sense that the effect by the filter itself on the light guided by the waveguide layer is minimized or practically avoided. Here it should be understood that the line openings having their longitudinal direction parallel with the direction of propagation DOP of light guided by the waveguide layer WGL is during operation of the planar waveguide device PWD when light is guided in the waveguide layer WGL.

Figure 2:
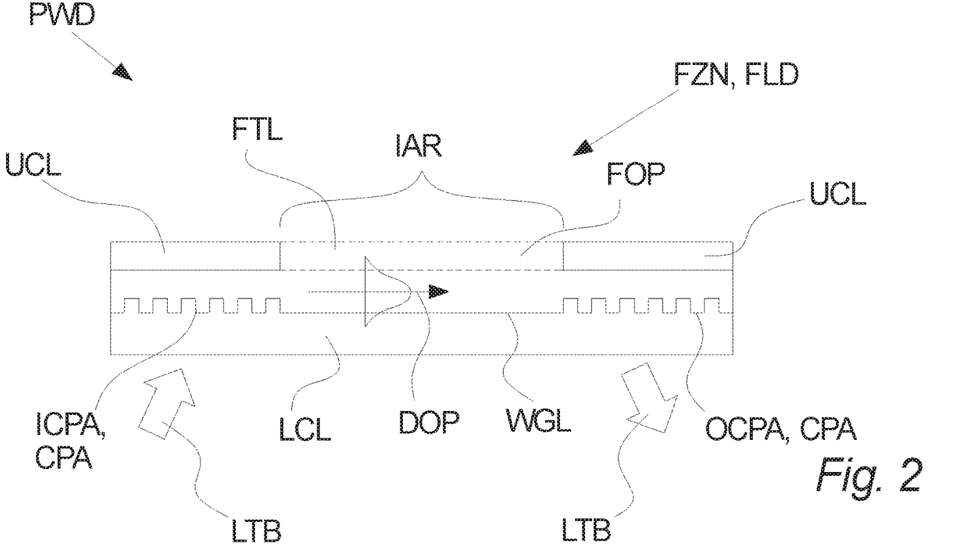
FIGS. 2-4 illustrate cross-section side views of planar waveguide devices according to embodiments of the invention.
Figure 5:
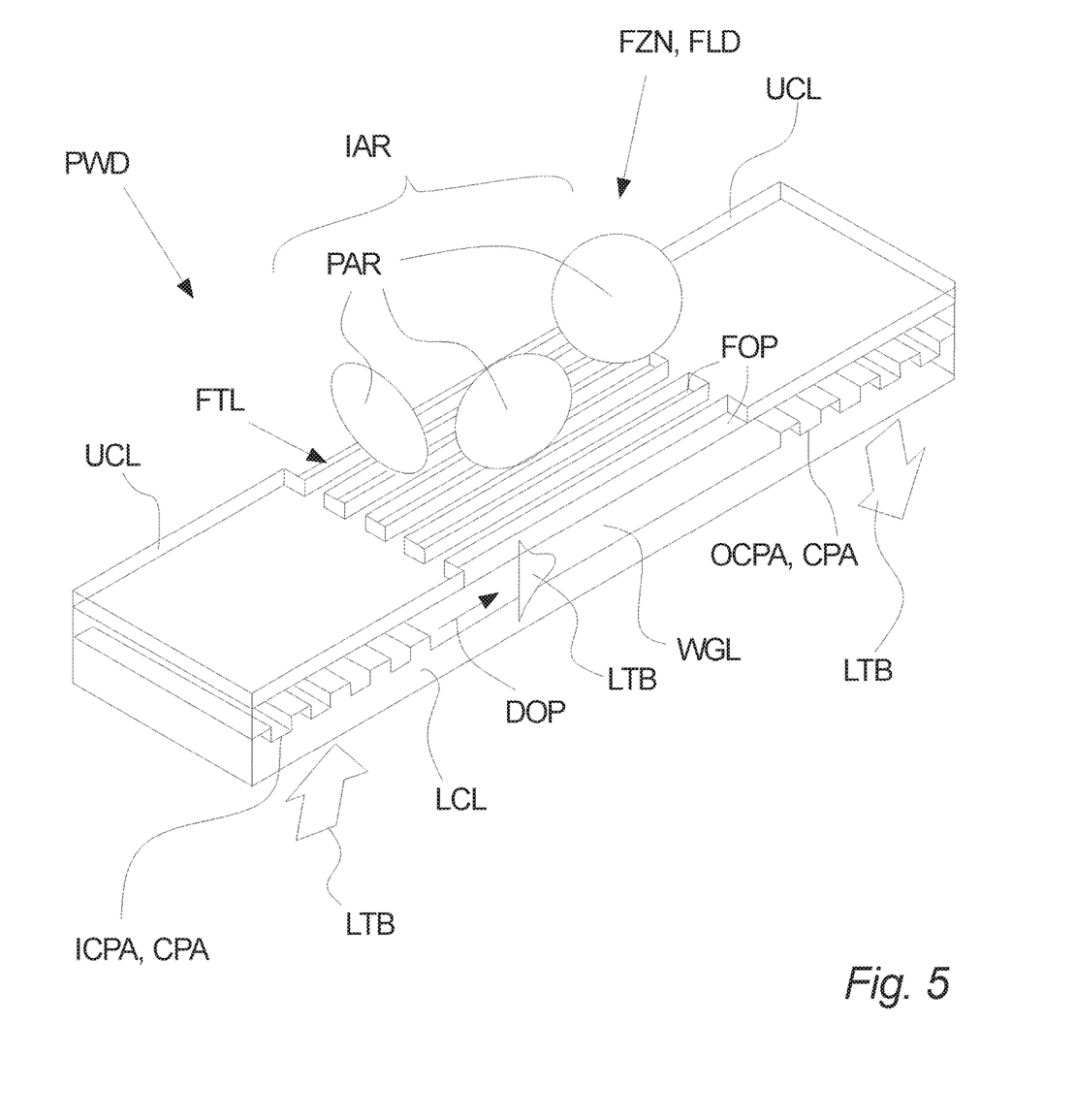
FIGS. 5-6 illustrate perspective views of planar waveguide devices according to an embodiments of the invention.

Now, referring to FIGS. 2 and 5, a planar waveguide device PWD according to a further embodiment of the invention is illustrated in a cross-sectional side view on FIG. 2 and in a perspective view on FIG. 5.

Further to what is illustrated on FIG. 1, the in-coupling arrangement CPA is here seen as being made up by two coupling elements; an in-coupling element ICPA, and an out-coupling element OCPA.

In FIGS. 2 and 5 the in-coupling element ICPA and the out-coupling element OCPA are both illustrated as gratings. However, in other embodiments the coupling elements may be provided by different means as mentioned with FIG. 1, and need not be the same, e.g. a prism may be used as an in-coupling element ICPA, and a grating may be used as an out-coupling element OCPA.

A light beam LTB is coupled into the waveguide layer WGL by means of the in-coupling element ICPA, then guided through the waveguide layer WGL in the direction of propagation DOP, passing by filter layer FTL in the interaction region IAR to the out-coupling element OCPA, where it is coupled out from the waveguide layer WGL.

Light source LSO and light sensor LSE are not illustrated on FIG. 2 or 5, but may be utilized as in FIG. 1.

As can be seen from both FIGS. 2 and 5, the interaction region IAR defined by the extent of the filter layer FTL extends between the in-coupling element ICPA and the out-coupling element OCPA, but not over any of these. Thus, the embodiment illustrated in FIGS. 2 and 5 is highly suitable for e.g. absorption and excitation interactions between the fluid and the evanescent field in the filter openings FOP. The area where the filter layer FTL does not extend, is covered by an upper cladding layer UCL to facilitate guiding in the waveguide layer WGL. Similarly, a lower cladding layer LCL is positioned below the waveguide layer WGL. Typically, the refractive indices the of the upper and lower cladding layer UCL, LCL are lower than the refractive index of the waveguide layer WGL.

In FIG. 5 the particles PAR not allowed to enter into the filter openings FOP and thus prevented from interacting with the evanescent field therein may represent red blood cells in a blood hemolysis sensor setup. However, they also illustrate the more general principle that particles having a size, e.g. a diameter, larger than a predefined size defined by the width of the filter openings FOP, are prevented from entering the filter openings FOP and interacting with the evanescent field.

It is noted that FIG. 5 is made partly see-through to help understand the composition of the varies elements of the illustrated planar waveguide device PWD.

Figure 3:
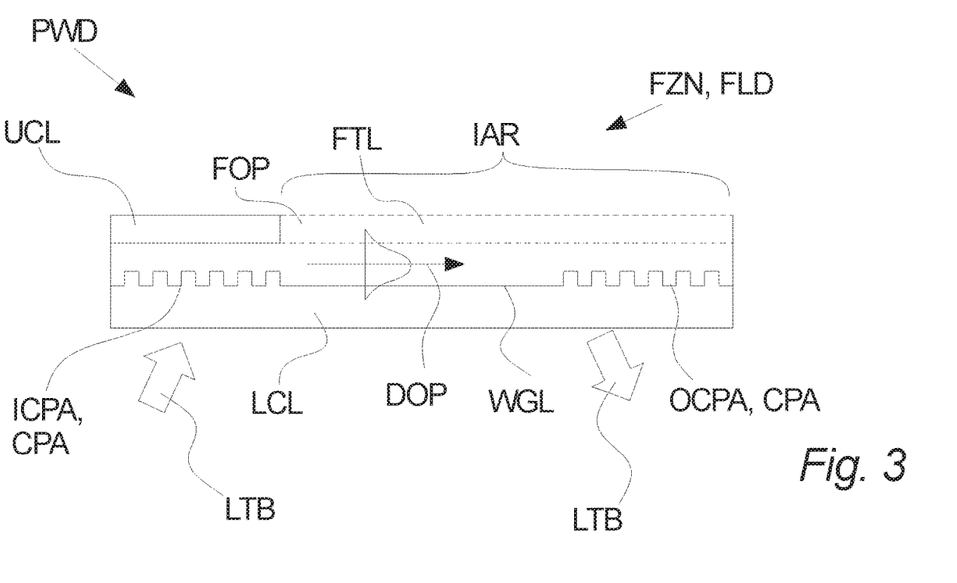

In FIG. 3 a slightly modified embodiment is illustrated in a cross-sectional side view. Here, the filter layer FTL extends also over the out-coupling element OCPA to allow interaction between the fluid and the evanescent field of the guided light during out-coupling. Since the planar waveguide device PWD illustrated on FIG. 3 has a guided distance along the filter layer FTL (i.e. the in-coupling element ICPA and the out-coupling elements OCPA are separated by some distance) the fluid FLD is allowed to interact with the evanescent field here, making it suitable for absorption and excitation interactions with the fluid. Since the filter layer FTL and this the interaction region IAR extends also over the out-coupling element OCPA, the illustrated planar waveguide device PWD is also suitable for providing information about the refractive index of the fluid FLD.

Figure 4:
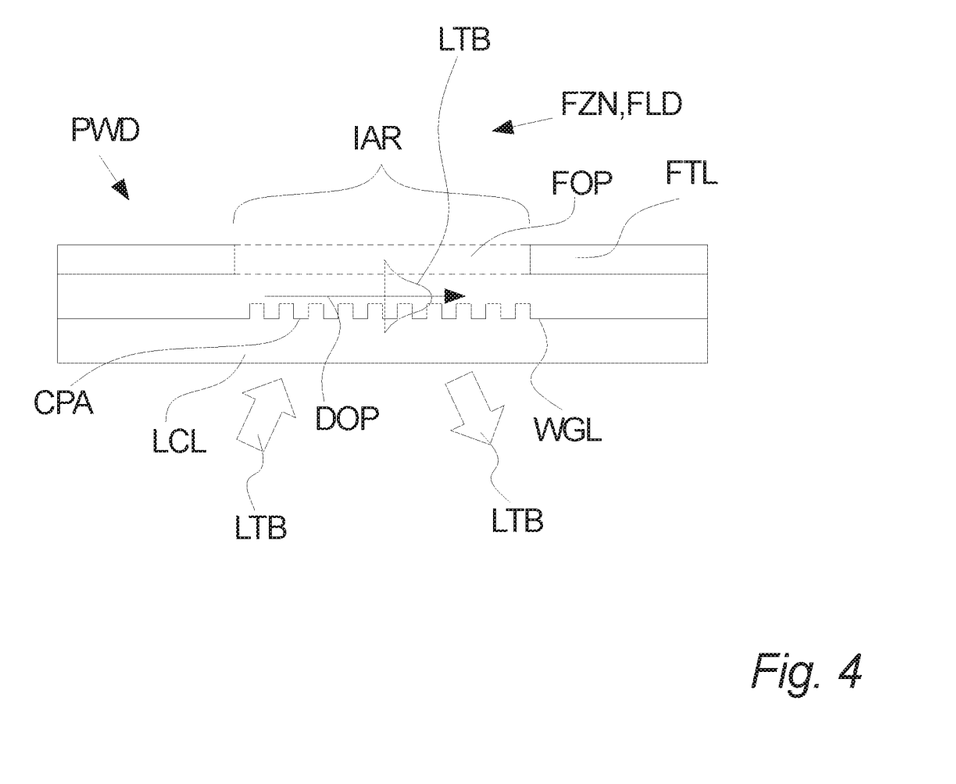
Figure 6:
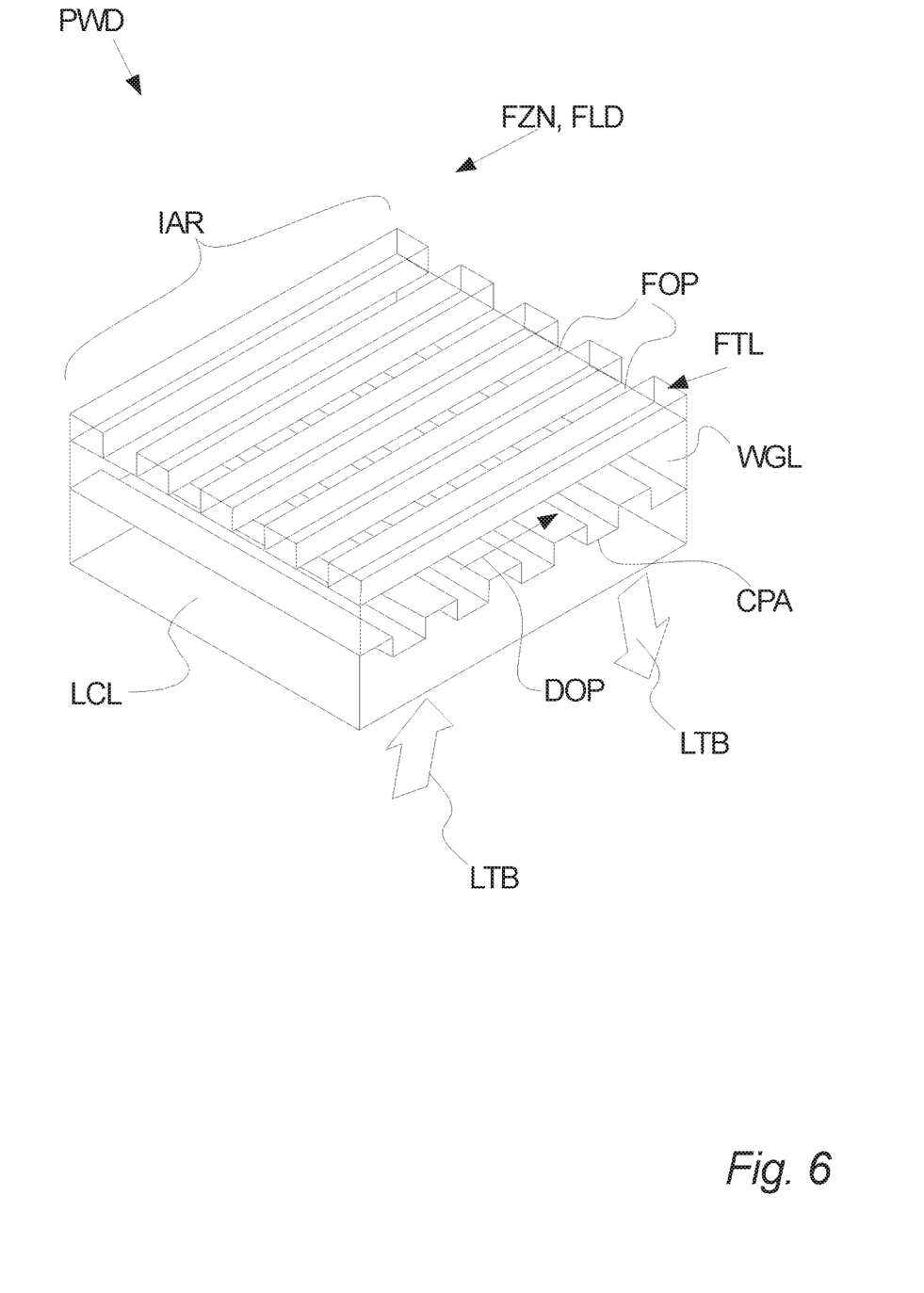

Now referring to FIGS. 4 and 6, two similar embodiments are illustrated. FIG. 4 illustrates a cross-sectional side view, while FIG. 6 illustrates a perspective view. While FIG. 6 illustrates only the interaction region IAR, FIG. 4 shows also the waveguide layer WGL extending a bit beyond that. In both embodiments, the coupling arrangement CPA is composed by a single coupling element thus providing both in-coupling of light into the waveguide layer WGL and out-coupling therefrom again. Since the out-coupling is performed within the interaction region IAR, the out-coupling is influenced by the refractive index of the fluid FLD, and thus the illustrated planar waveguide devices PWD are suitable for measurement of the refractive index of the fluid FLD.

It is noted that FIG. 6 is made partly see-through to help understand the composition of the varies elements of the illustrated planar waveguide device PWD.

Figure 7:
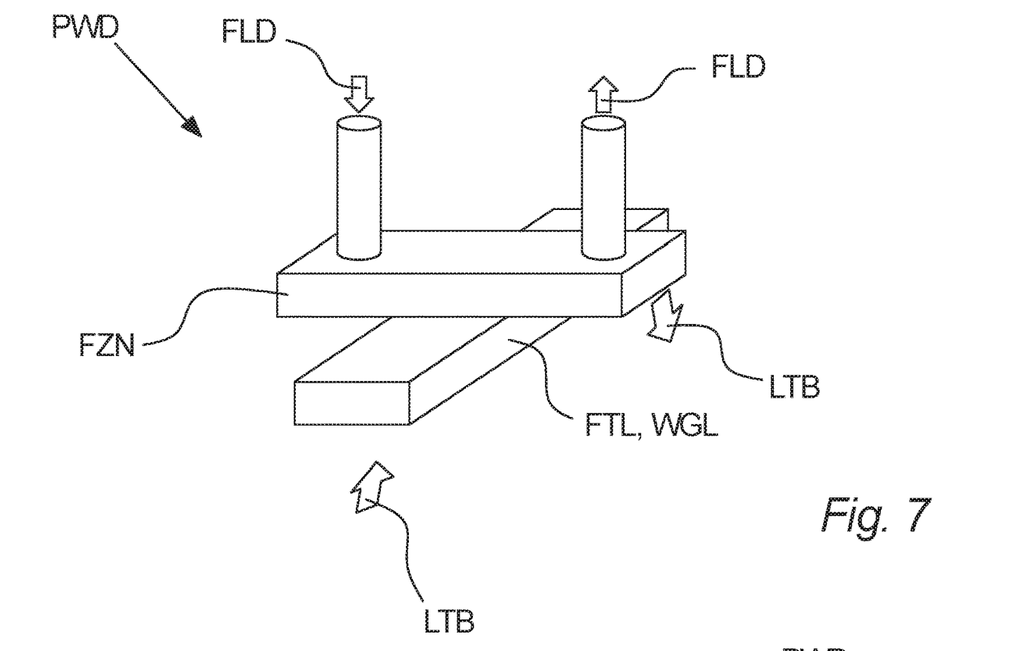
FIG. 7 illustrates a planar waveguide device according to an embodiment of the invention.

Referring to FIG. 7, a planar waveguide device PWD according to an embodiment of the invention is illustrated. The planar waveguide device PWD comprises a filter layer FTL and waveguide layer WGL, e.g. as described in relation to FIGS. 1 and 5. The fluid zone FZN is formed as a fluid channel extending so as to facilitate a flow of fluid coming into contact with the filter layer FTL. In FIG. 7, the direction of the fluid flow is approximately perpendicular to the direction of propagation of light, whereas in other embodiments the relative angle may be e.g. approximately 45 degrees or 0, i.e. a parallel configuration. In FIG. 7, the fluid to be measured is supplied to the fluid zone FZN and extracted therefrom again by suitable tubes. This illustrates that in the context of FIG. 7, the fluid is provided continuously to the planar waveguide device PWD, preferably by a relatively steady flow rate, in contrast to e.g. a fluid flow dictated by surroundings when using the planar waveguide device PWD submerged in an environmental situation (i.e. not in the laboratory), or when fluid flow is approximately zero.

Figure 8:
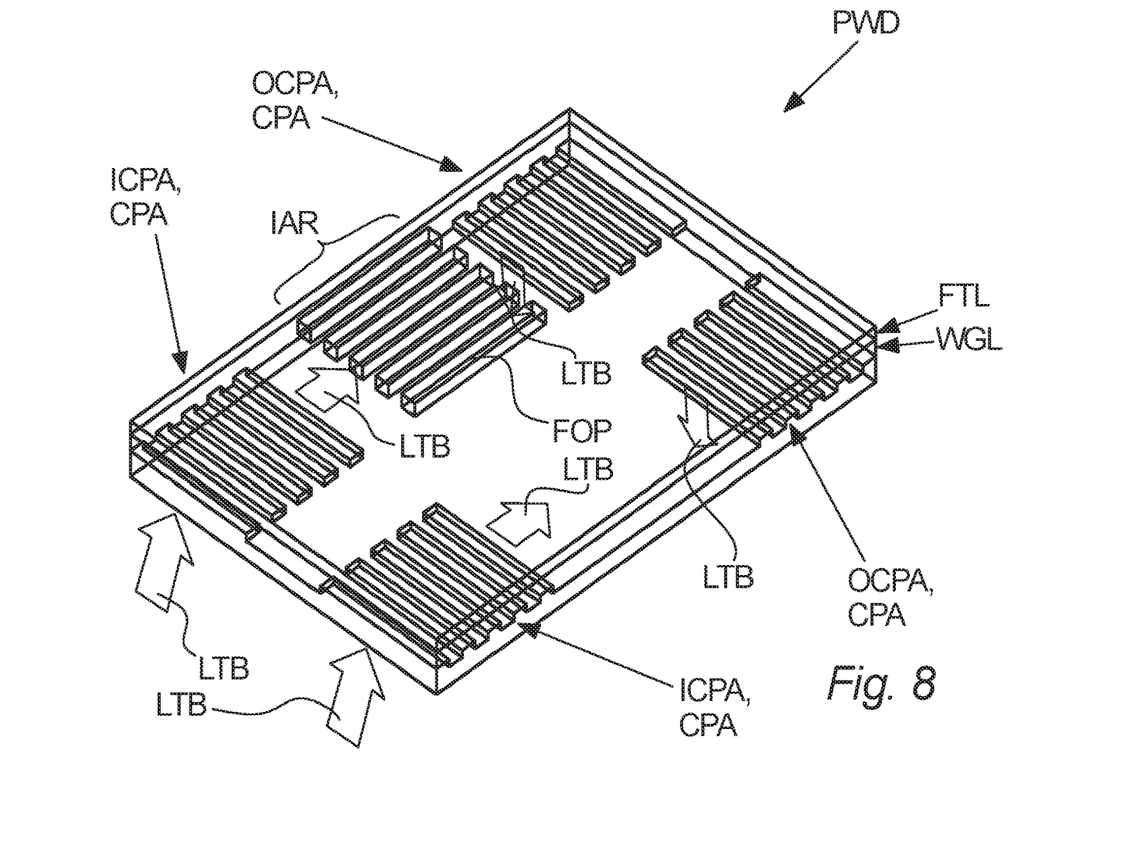
FIG. 8 illustrates a planar waveguide device according to an embodiment of the invention.

Referring to FIG. 8, a planar waveguide device PWD according to an embodiment of the invention is illustrated. It is noted that FIG. 8 is made partly see-through to help understand the composition of the varies elements of the illustrated planar waveguide device PWD.

In this embodiment, the planar waveguide device PWD comprises two paths for light, the upper left path being similar to that described in relation to FIGS. 1 and 5, the lower right being identical only that no filter openings are present in the filter layer FTL.

This allows the light to be sent by two substantially identical paths with the difference that light is interacted with a fluid in the upper left path but not in the lower left path.

In one embodiment, the same light source is used for each path, e.g. by utilizing a double slit to split the original light beam into two. After outcoupling of the light beams from each of the two paths, the two outcoupled light beams may be interacted e.g. by interference. This may for example be done using another double slit to create an interference pattern, or by using modified output coupling arrangement, e.g. a modified grating coupler arrangement. By means of this setup, changes in refractive index of the fluid may be measured.

EXAMPLES

A planar waveguide device was excited with a 532 nanometer laser through grating couplers. The image of the fluid zone in the form of a flow channel is captured with a CMOS camera through a microscope objective. A fluorescent emission filter was used in between to eliminate the excitation wavelength. The waveguide device comprises a filter layer according to the invention with a filter opening having a width of 200-220 nanometer and with a 400 nanometer periodicity.

An autofluorescence pattern is generated by the self-fluorescence of the waveguide polymer, where the light is travelling in a direction corresponding to vertically through the image and the fluid flow is perpendicular to the light propagation. The result of the autofluorescence is shown in FIG. 9A.

Two types of polystyrene red fluorescent beads with different diameters (100 nanometer and 2 micrometer) in aqueous suspension were used to characterize the size exclusion function. Both were red fluorescent and used with 0.1% solid concentration. The results are shown in FIG. 9B (2 micrometer beads) and FIG. 9C (100 nanometer beads). Also, the results of FIG. 9A-9C are shown in a comparable manner in FIG. 9D, showing the normalized fluorescence intensity for each of the three measurements as a function of the distance across the waveguide (in micrometers).

These results demonstrated much stronger fluorescent response from the 100 nm beads, i.e. they are excited by the waveguide evanescent field. The 2 um beads can be only excited with scattering light from the waveguide.

Figure 9A:
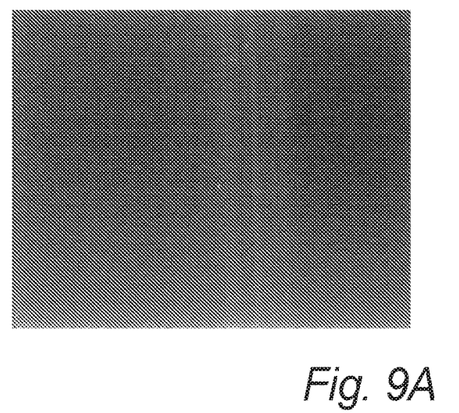
FIGS. 9A-9D and 10 illustrate experimental data obtained using a planar waveguide device of the invention.
Figure 9B:
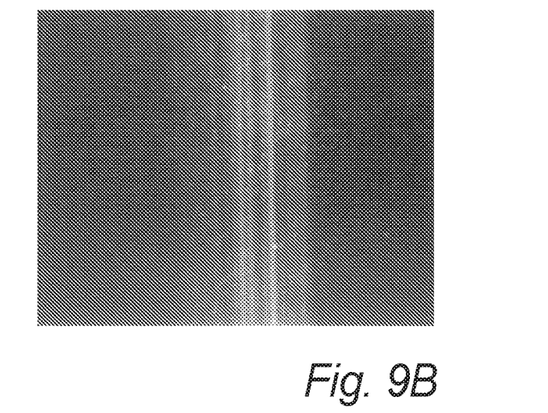
Figure 9C:
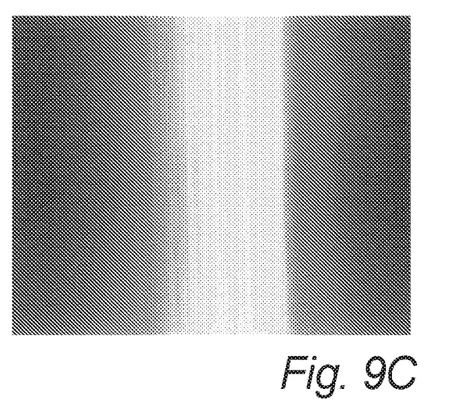
Figure 9D:
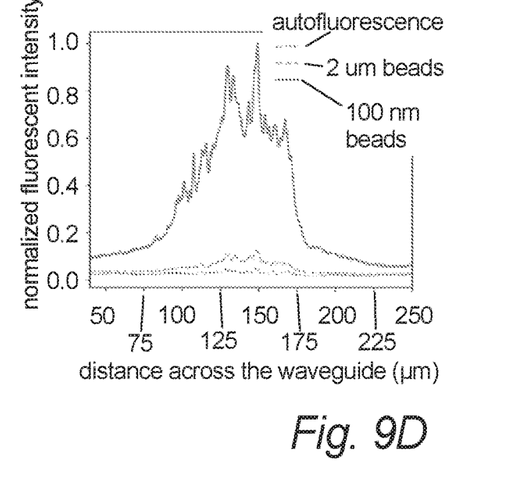

Thus, FIGS. 9A-C and corresponding FIG. 9D demonstrate a selective interaction between the planar waveguide device and particles, where particles with a diameter larger than a predefined size are prevented from interacting with the light of the waveguide device.

Figure 10:
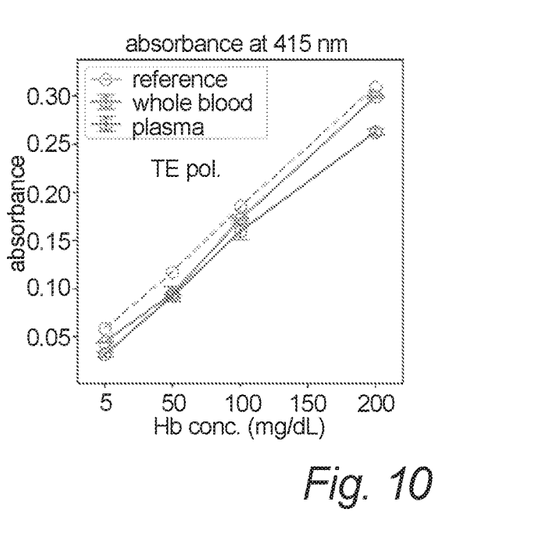

In FIG. 10, measurements of different hemoglobin (Hb) concentrations in whole blood (WB) and plasma are shown. The photo-spectrometer reference spectra are scaled and plotted at the background. In more detail, FIG. 10 shows the measurements of whole blood samples (middle line) and their plasma counterparts (bottom line) as well as the photo-spectrometer reference measurements with 1 cm cuvettes (upper gray dashed line), where the latter is scaled in amplitude for comparison. The maximum Hb concentration used is 200 mg/dL, which corresponds to about 0.7% hemolysis. Each data point is based on three measurements. At 0 and 100 mg/dL Hb concentrations, the coefficients of variation (CoV) are 1.65% and 0.86%, respectively, showing excellent repeatability of the sensor. On the other hand, comparing the whole blood and plasma measurements, we observed very good overlaps which shows that filtration is highly effective. The absorbance of the WB samples is slightly higher than that of the plasma, which can be attributed to the unspecific scattering of the light which can be absorbed by red blood cells in the bulk.

FIGURE REFERENCES

PWD. Planar waveguide device
FLD. Fluid
WGL. Waveguide layer
CPA. Coupling arrangement
FTL. Filter layer
ICPA. In-coupling element
OCPA. Out-coupling element
FZN. Fluid zone
IAR. Interaction region
FOP. Filter openings
PAR. Particles
DOP. Direction of propagation
LCL. Lower cladding layer
UCL. Upper cladding layer
LSE. Light sensor
LSO. Light source
LTB. Light beam

The invention claimed is:

1. A planar waveguide device for interacting with a fluid, the planar waveguide device comprising
   a waveguide layer for supporting optical confinement,
   a coupling arrangement for in-coupling and out-coupling of light into and from the waveguide layer,
   a fluid zone for accommodating the fluid,
   a filter layer arranged between the fluid zone and the waveguide layer in an interaction region (IAR) of the waveguide layer, wherein the filter layer comprises filter openings arranged to allow the fluid to interact with an evanescent field of light guided by the waveguide layer,
   wherein the filter openings are adapted to prevent particles larger than a predefined size from interacting with said evanescent field,
   wherein the filter openings are arranged as line openings having their longitudinal direction in parallel with the direction of propagation of light guided by the waveguide layer,
   wherein the planar waveguide device further comprises a cladding layer adjacent to the waveguide layer,
   wherein the cladding layer has a refractive index lower than that of the waveguide layer, and
   wherein the cladding layer and the filter layer are made from the same material.

2. The planar waveguide device according to claim 1, wherein the filter openings are defined by a line spacing of at most 10 micrometer.

3. The planar waveguide device according to claim 2, wherein the filter openings are defined by a line spacing of at most 5 micrometer, at most 1 micrometer, at most 800 nanometer, at most 200 nanometer, or at most 100 nanometer.

4. The planar waveguide device according to claim 1, wherein said coupling arrangement comprises an in-coupling element for in-coupling of light into the waveguide layer and an out-coupling element for out-coupling of light from the waveguide layer, and wherein the interaction region extends between the in-coupling element and the out-coupling element.

5. The planar waveguide device according to claim 1, wherein said coupling arrangement comprises an in-coupling element for in-coupling of light into the waveguide layer and an out-coupling element for out-coupling of light from the waveguide layer, and wherein the interaction region extends between the in-coupling element and the out-coupling element and also over the out-coupling element.

6. The planar waveguide device according to claim 1, wherein said coupling arrangement extends over at least part of the interaction region.

7. The planar waveguide device according to claim 6, wherein said coupling arrangement extends over the whole of the interaction region.

8. The planar waveguide device according to claim 1, wherein the out-coupling element comprises a dispersive element.

9. The planar waveguide device according to claim 8, wherein the dispersive element is a grating.

10. The planar waveguide device according to claim 1, wherein the planar waveguide device further comprises a laser device as a light source.

11. The planar waveguide device according to claim 1, wherein the planar waveguide device further comprises a broadband light source as a light source.

12. The planar waveguide device according to claim 1, wherein the planar waveguide device further comprises an array based light sensor.

13. The planar waveguide device according to claim 12, wherein the array based light sensor is a CMOS sensor, CCD sensor, or photodiode array sensor.

14. The planar waveguide device according to claim 1, wherein the planar waveguide device further comprises an optical spectrometer as a light sensor.

15. The planar waveguide device according to claim 1, wherein the fluid is a liquid.

16. The planar waveguide device according to claim 1, wherein the planar waveguide device further comprises a fluid flow channel forming the fluid zone.

17. The planar waveguide device according to claim 1, wherein the fluid flow channel is a flow cell.

18. A method of detecting blood hemolysis, the method comprising using a planar waveguide device according to claim 1.

19. A method of interacting light with a fluid, the method comprising coupling light into a waveguide layer, guiding light within the waveguide layer forming an evanescent field outside the waveguide layer, interacting the evanescent field of guided light with the fluid, filtering the fluid so as to prevent particles larger than a predefined size from interacting with said evanescent field using a filter layer comprising filter openings arranged to allow the fluid to interact with an evanescent field of light guided by the waveguide layer, coupling interacted light out from the waveguide layer, wherein the filter openings are arranged as line openings having their longitudinal direction in parallel with the direction of propagation of light guided by the waveguide layer.

20. The method according to claim 19, wherein the method further comprises measuring at least one characteristic of the outcoupled light.

* * * * *

UNITED STATES PATENT AND TRADEMARK OFFICE
CERTIFICATE OF CORRECTION

PATENT NO.        : 11,255,780 B2
APPLICATION NO.   : 16/489762
DATED             : February 22, 2022
INVENTOR(S)       : Anders Kristensen et al.

It is certified that error appears in the above-identified patent and that said Letters Patent is hereby corrected as shown below:

On the Title Page

Item (30), Foreign Application Priority Data, "17158711" should read as --17158711.6--.

Signed and Sealed this
Thirty-first Day of May, 2022

Katherine Kelly Vidal
*Director of the United States Patent and Trademark Office*